US010818468B1

(12) United States Patent
Hansson et al.

(10) Patent No.: US 10,818,468 B1
(45) Date of Patent: Oct. 27, 2020

(54) LIQUID TARGET X-RAY SOURCE WITH JET MIXING TOOL

(71) Applicant: Excillum AB, Kista (SE)

(72) Inventors: Björn Hansson, Kista (SE); Tomi Tuohimaa, Kista (SE); Göran Johansson, Kista (SE)

(73) Assignee: EXCILLUM AB, Kista (SE)

( * ) Notice: Subject to any disclaimer, the term of this patent is extended or adjusted under 35 U.S.C. 154(b) by 322 days.

(21) Appl. No.: 16/081,585

(22) PCT Filed: Mar. 1, 2017

(86) PCT No.: PCT/EP2017/054752
§ 371 (c)(1),
(2) Date: Aug. 31, 2018

(87) PCT Pub. No.: WO2017/149006
PCT Pub. Date: Sep. 8, 2017

(30) Foreign Application Priority Data

Mar. 1, 2016 (EP) .................................... 16158038

(51) Int. Cl.
*A61B 6/00* (2006.01)
*H01J 35/18* (2006.01)
(Continued)

(52) U.S. Cl.
CPC .............. *H01J 35/18* (2013.01); *H01J 35/06* (2013.01); *H01J 35/14* (2013.01); *H01J 2235/082* (2013.01)

(58) Field of Classification Search
CPC .. H01J 35/18; H01J 35/14; H01J 35/06; H01J 2235/082
See application file for complete search history.

(56) References Cited

U.S. PATENT DOCUMENTS 4,953,191 A 8/1990 Smither et al.
2017/0345611 A1* 11/2017 Heid .................... H01J 35/065

FOREIGN PATENT DOCUMENTS

WO 2010083854 A1 7/2010
WO 2013185829 A1 12/2013

OTHER PUBLICATIONS

International Search Report (PCT/ISA/210) dated May 15, 2017, by the European Patent Office as the International Searching Authority for International Application No. PCT/EP2017/054752.

(Continued)

*Primary Examiner* — Kiho Kim
(74) *Attorney, Agent, or Firm* — Buchanan Ingersoll & Rooney P.C.

(57) ABSTRACT

An X-ray source and a corresponding method for generating X-ray radiation are disclosed. The X-ray source includes a target generator, an electron source and a mixing tool. The target generator is adapted to form a liquid jet propagating through an interaction region, whereas the electron source is adapted to provide an electron beam directed towards the interaction region such that the electron beam interacts with the liquid jet to generate X-ray radiation. The mixing tool is adapted to induce mixing of the liquid jet at a distance downstream of the interaction region such that a maximum surface temperature of the liquid jet is below a threshold temperature. By controlling the maximum surface temperature, vaporisation, and thus the amount of contaminations originating from the jet, may be reduced.

19 Claims, 6 Drawing Sheets

(51) Int. Cl.
*H01J 35/14* (2006.01)
*H01J 35/06* (2006.01)

(56) References Cited

OTHER PUBLICATIONS

Written Opinion (PCT/ISA/237) dated May 15, 2017, by the European Patent Office as the International Searching Authority for International Application No. PCT/EP2017/054752.
Otendal, M., et al., "Stability and debris in high-brightness liquid-metal-jet-anode microfocus x-ray sources", Journal of Applied Physics, vol. 101, No. 2 , pp. 26102-1 to 026102-3.

* cited by examiner

LIQUID TARGET X-RAY SOURCE WITH JET MIXING TOOL

TECHNICAL FIELD

The invention disclosed herein generally relates to electron impact X-ray sources. In particular, it relates to an X-ray source utilising a liquid jet as a target and a jet mixing tool for temperature control.

BACKGROUND

Systems for generating X-rays by irradiating a liquid target are described in the applicant's International Applications PCT/EP2012/061352 and PCT/EP2009/000481. In these systems, an electron gun comprising a high-voltage cathode is utilised to produce an electron beam that impinges on a liquid jet. The target is preferably formed by a liquid metal with low melting point, such as indium, tin, gallium lead or bismuth, or an alloy thereof, provided inside a vacuum chamber. Means of providing the liquid jet may include a heater and/or cooler, a pressurising means (such as a mechanical pump or a source of chemically inert propellant gas), a nozzle and a receptacle to collect liquid at the end of the jet. The position in space wherein a portion of the liquid jet is hit by the electron beam during operation is referred to as the interaction region or interaction point. The X-ray radiation generated by the interaction between the electron beam and the liquid jet may leave the vacuum chamber through a window separating the vacuum chamber from the ambient atmosphere.

During operation of the X-ray source, free particles, including debris and vapour from the liquid jet, tend to deposit on the window and the cathode. This causes a gradual degradation of the performance of the system, as depositing debris may obscure the window and reduce the efficiency of the cathode. In PCT/EP2012/061352, the cathode is protected by an electric field arranged to deflect charged particles moving towards the cathode. In PCT/EP2009/000481, a heat source is employed to evaporate contaminants deposited on the window.

Even though such technologies may mitigate the problems caused by contaminants in the vacuum chamber, there is still a need for improved X-ray sources having increased useful life as well as increased maintenance intervals.

SUMMARY

It is an object of the present invention to provide an X-ray source addressing at least some of the above shortcomings. A particular object is to provide an X-ray source requiring less maintenance and having an increased useful life.

This and other objects of the technology disclosed are achieved by means of an X-ray source and a method having the features defined in the independent claims. Advantageous embodiments are defined in the dependent claims.

Hence, according to a first aspect of the invention, there is provided an X-ray source comprising a target generator, an electron source and a mixing tool. The target generator is adapted to form a liquid jet propagating through an interaction region, whereas the electron source is adapted to provide an electron beam directed towards the interaction region such that the electron beam interacts with the liquid jet to generate X-ray radiation. In the present aspect, the mixing tool is adapted to induce mixing of the liquid jet at a distance downstream of the interaction region such that a maximum surface temperature of the liquid jet downstream of the interaction region is below a threshold temperature.

According to a second aspect, a corresponding method for generating X-ray radiation is provided. The method comprises the steps of forming a liquid jet propagating through an interaction region, directing an electron beam towards the liquid jet such that the electron beam interacts with the target jet at the interaction region to generate X-ray radiation, and induce, by means of a mixing tool, mixing of the liquid jet. The mixing is induced at a distance downstream of the interaction region such that a maximum temperature of the jet downstream of the interaction region is below a threshold temperature.

The mixing tool may be realised by an edge or surface adapted to disturb or interact with the liquid jet at a distance downstream of the interaction region. The liquid jet may thereby be mixed internally, i.e., within the jet, such that the maximum surface temperature is kept below the threshold. Alternatively, or additionally, the mixing tool may be realised by a liquid source arranged to supply or add additional liquid to the liquid jet at said distance. The supply of the additional liquid may induce mixing or stirring of the liquid of the jet such that portions of the jet that are heated by the interaction between the liquid and the electron beam may be cooled by other, less heated or cooler portions of the jet and/or by the additional liquid. In other words, a local temperature gradient in the jet may be modified by mixing the within the jet such that the maximum surface temperature of the liquid jet downstream of the interaction region is kept below the threshold temperature. Further, the additional liquid may in some examples form a coating or cover encapsulating at least a portion of the liquid jet so as to reduce the surface temperature or at least keep it below the threshold temperature. In other examples, the additional liquid may provide a reservoir in which the liquid of the jet may be buried, submerged or mixed, thereby allowing the temperature of the liquid of the jet to be kept below the threshold temperature. The term 'additional liquid' should be understood as liquid not forming part of the jet at the interaction region, or, in other words, any liquid added to the jet downstream of the interaction region.

The present invention is based on the realisation that a surprisingly high percentage of contaminants, in particular originating from vapour from the liquid jet, originate from the surface of the liquid jet downstream of the interaction region. The inventors have found that the degree of vaporisation of the liquid depends, inter alia, on the surface temperature of the liquid jet, and that a maximum temperature of the surface is located at a certain distance downstream of the interaction region. At this certain distance, a vaporisation maximum from the surface is believed to occur. Hence, by controlling the surface temperature downstream of the interaction region, the vaporisation, and thus the amount of contamination, may be reduced. In particular, the maximum surface temperature may be kept below a threshold value so as to mitigate formation of vapour from the surface of the liquid jet.

In the present aspects, mixing of the liquid jet is used to control or reduce the maximum surface temperature downstream of the interaction region. The temperature control or reduction may be realised by adding liquid to the jet downstream of the interaction region so as to absorb at least some of the heat induced by the interaction between the electron beam and liquid at the interaction region, or by mixing or stirring the liquid of the jet internally so as to promote convection of the induced heat to less heated portions of the jet.

Without acquiescing to a particular physical model, the distance between the interaction region and the location of the maximum surface temperature of the jet is believed to depend on parameters such as penetration depth of the electron beam into the liquid jet, the electron velocity in the liquid, the velocity of the liquid jet, and the heat diffusivity of the liquid. As the electrons impact the liquid at the interaction region, they will penetrate to a certain depth within the jet and thereby cause the temperature inside the jet to increase. The induced heat tends to diffuse towards the surface of the jet as the jet, due to its velocity, propagates in a downstream direction. Consequently, the surface temperature of the jet may increase with the distance from the interaction region until a maximum surface temperature is reached. The time it takes for the heat to dissipate to the surface will, together with the velocity of the jet, affect the downstream distance between the interaction region and the location of the maximum surface temperature.

Vaporisation should, in the context of the present application, be understood as a phase transition of the liquid from the liquid phase to vapour. Evaporation and boiling are two examples of such a transition. Boiling may occur at or above the boiling temperature of the liquid, whereas evaporation may occur at temperatures below the boiling temperature for a given pressure. Evaporation may occur when the partial pressure of vapour of the liquid is less than the equilibrium vapour pressure, and may in particular occur at the surface of the jet.

Considering these definitions, the threshold temperature may e.g. be determined based on the actual boiling temperature of the liquid of the jet, the partial pressure of the vapour, or the equilibrium vapour pressure within the vacuum chamber. Alternatively, or additionally, the threshold may be determined based on empirical studies of acceptable vaporisation levels for specific systems, desired maintenance intervals, operational modes of the X-ray source, or performance requirements. In one example, the threshold may correspond to the potential maximum temperature that can be generated by the heat impacting electron beam. In general, the degree of vaporisation increases with the surface temperature and may thus be controlled by controlling the surface temperature.

From one point of view, it is desirable to add the additional liquid (and/or cause the liquid of the jet to be mixed) as close to the interaction region as possible so as to ensure that the surface temperature does not have enough time to reach the threshold temperature and to minimize or at least reduce the surface emitting vapour. From another point of view, it is desirable to add the additional liquid (and/or mix the jet) at a position as far away from the interaction point as possible so as to reduce the risk of affecting or disturbing the interaction region. Regardless of the above points, the position at which the liquid is added (and/or the liquid jet is mixed) should preferably be selected such that the maximum potential surface temperature, caused by diffusion of heat to the surface, not occurs between the said position and the interaction region.

It will be appreciated that the liquid for the jet may be a liquid metal, such as e.g. indium, tin, gallium, lead or bismuth, or an alloy thereof. Further examples of liquids include e.g. water and methanol.

The term 'liquid jet' or 'target' may, in the context of the present application, refer to a stream or flow of liquid being forced through e.g. a nozzle and propagating through the interior of the vacuum chamber. Even though the jet in general may be formed of an essentially continuous flow or stream of liquid, it will be appreciated that the jet additionally, or alternatively, may comprise or even be formed of a plurality of droplets. In particular, droplets may be generated upon interaction with the electron beam. Such examples of groups or clusters of droplets may also be encompassed by the term 'liquid jet' or 'target'.

Advantageous embodiments of the invention as defined by the dependent claims will now be briefly discussed. A first group of embodiments relates to X-ray sources in which the mixing tool is formed by an edge or surface interacting with the liquid jet. A second group of embodiments relate to a mixing tool realised by a liquid source comprising a pool of additional liquid. The pool may be arranged such that a surface of the pool, on which the liquid jet impinges, is positioned at such a distance downstream of the interaction region that the maximum surface temperature is allowed to be kept below the threshold temperature. A third group of embodiments utilise a mixing tool wherein an additional liquid jet is mixed with the liquid jet target at a downstream distance preventing the maximum surface temperature from reaching, and passing, the threshold temperature.

According to an embodiment, the mixing tool may comprise a surface arranged to intersect the liquid jet. In other words, the liquid jet may, during operation, impact the surface which may be a slanting surface relative to the liquid jet. By arranging the surface such that the liquid jet impacts on the surface at the above-mentioned distance downstream of the interaction region, mixing of the liquid jet may be induced so as to keep the maximum surface temperature below the threshold temperature.

According to an embodiment, the mixing tool is a liquid source adapted to supply an additional liquid to the liquid jet. The additional liquid may be of the same type of liquid as the liquid jet, or a different type. Suitable additional liquids may include e.g. liquid metals, water and methanol. Advantageously, a temperature of the additional liquid may be equal to or lower than a temperature of the liquid jet upstream of the interaction region. In case the temperature of the additional liquid is similar to the liquid forming the jet, they may both be pumped or handled by a system that is at least partly common to both. Thus, the complexity and cost of the system may be reduced. Using an additional liquid of a temperature that is lower than the temperature of the liquid jet upstream of the interaction region is advantageous in that the cooling efficiency may be increased. Increasing the cooling efficiency may further reduce the amount, or flow of additional liquid required for achieving the desired temperature controlling effect.

According to an embodiment, the liquid source is formed by a pool of the additional liquid. When comparing to an additional jet, the pool allows for a larger amount of additional liquid to be supplied more or less instantly to the liquid jet. This further allows for a faster cooling of the liquid jet, and hence a reduced amount of vapour.

According to an embodiment, the X-ray source may comprise a sensor for measuring a level of the additional liquid of the pool, and a level controlling device for controlling the level based on output from the sensor. Thus, a level control may be achieved so as to improve the accuracy and control of the distance between the interaction region and the position at which the additional in the pool is supplied to, or mixed with the liquid jet. The sensor may utilise a direct measurement of the liquid level of the pool, or an indirect observation based on e.g. the flow out of the pool. The level controlling device may operate in response to a signal from the sensor, and may e.g. be realised by increasing or reducing the amount or rate of liquid discharged from the pool.

According to an embodiment, the liquid source may be adapted to supply the additional liquid in the form of an additional jet. The additional jet may be directed to intersect with the liquid jet target at the desired distance downstream of the interaction point. Upon impact, the jets may mix with each other and form a single jet propagating in the downstream direction.

The liquid source may be adapted to align the additional jet with the target so as to increase the cooling efficiency and positioning on the target, and to reduce the risk for splatter and debris generated upon impact.

According to an embodiment, a velocity of the additional jet may comprise a non-negative component in respect to a travelling direction of the liquid jet so as to facilitate the mixing with the liquid jet target and to further reduce the risk of splatter and debris. Such an oblique angle of impact may also reduce the risk of the additional jet affecting the interaction region.

According to an embodiment, the liquid source may be adapted to supply the additional liquid to the liquid jet in the form of a liquid curtain. This may for example be realised by letting the additional liquid form a sheet or film, i.e., a body having an essentially two-dimensional extension, which the liquid jet may intersect or impinge on. The interaction between the liquid jet and the liquid curtain may result in the liquid jet merging with the curtain or at least partly passing therethrough. The additional liquid may propagate in a vertical direction, e.g. making use of the gravitation as primary accelerating force, or in a direction intersecting the vertical direction. Providing the additional liquid in the form of a liquid curtain increases the possible collision area, which makes it easier to hit by the liquid jet. Further, the liquid curtain may act as a shield limiting or even preventing migration of e.g. contaminants through the curtain. Thus, the liquid curtain may be used for retaining e.g. splashes and debris generated in the X-ray source.

According to an embodiment, the X-ray source may further comprise a shield arranged downstream of the interaction region. The shield may comprise an aperture arranged to allow the liquid jet to pass through the aperture. The shield may be provided for retaining splashes and debris generated downstream of the shield, e.g. from a receptacle collecting the jet. Instead of spreading in the vacuum chamber, depositing on the electron source, disturbing the interaction region or depositing on the window, the splashes and debris may deposit on an underside of the shield, i.e., the downstream side of the shield.

The shield and the aperture may be arranged in such manner in relation to the liquid jet that the velocity of the jet in the interaction region has a component perpendicular to the direction of gravity. In this way splashes and debris of liquid generated downstream of the shield may be directed away from the interaction region to further reduce the risk of contaminating the vacuum chamber and the different components located therein. When making such an arrangement, e.g. by providing the target liquid jet in a direction with an angle with respect to the direction of gravity, it is advantageous to arrange the electron beam so that it is essentially perpendicular to the surface of the liquid jet on impact so as to maximise, or at least increase, the X-ray generation efficiency.

According to an embodiment, the aperture may be arranged between the interaction region and the position of the liquid jet at which the additional liquid is supplied to the liquid jet so as to hinder splashes or debris generated by the impacting jets from affecting the interaction region and/or spreading in the vacuum chamber.

According to an embodiment, the X-ray source may comprise a sensor for detecting contamination, originating from the liquid of the jet, on the side of the shield facing away from the interaction region. The sensor allows for clogging of the aperture to be detected.

According to an embodiment, the shield may be arranged on a collection reservoir for collecting the liquid jet.

According to an embodiment, the additional jet may be arranged in such a manner as to not interfere with a line of sight between the interaction region and a charge collection sensor in the direction of the electron beam. The charge collection sensor may be used to detect the position or orientation of the target liquid jet as the electron beam is scanned over the jet and to detect when electrons reach the sensor and when the beam is blocked by the jet. In this way it is possible to accurately adjust the electron beam focusing and thus the size of the interaction region.

According to an embodiment, the X-ray source may further comprise, or be arranged in, a system comprising a closed-loop circulation system. The circulation system may be located between the collection reservoir and the target generator and may be adapted to circulate the collected liquid of the liquid jet and/or the additional liquid to the target generator. The closed-loop circulation system allows for continuous operation of the X-ray source, as the liquid may be reused. The closed-loop circulation system may be operated according to the following example:

- The pressure of liquid contained in a first portion of a closed-loop circulation system is raised to at least 10 bar, preferably at least 50 bar or more, using a high-pressure pump.
- The pressurised liquid is conducted to a nozzle. Although any conduction through a conduit will entail some, possibly negligible under the circumstances, loss of pressure, the pressurised liquid reaches the nozzle at a pressure still above 10 bar, preferably above 50 bar.
- The liquid is ejected from the nozzle into a vacuum chamber, in which the interaction region is located, for generating a liquid jet.
- The ejected liquid is collected in a collection reservoir after passage through the interaction region.
- The pressure of the collected liquid is raised to a suction side pressure (inlet pressure) for the high-pressure pump, in a second portion of the closed-loop circulation system located between the collection reservoir and the high-pressure pump in the flow direction (i.e., during normal operation of the system, liquid flows from the collection reservoir towards the high-pressure pump). The inlet pressure for the high-pressure pump is at least 0.1 bar, preferably at least 0.2 bar, in order to provide reliable and stable operation of the high-pressure pump.

The steps are then typically repeated continuously—that is, the liquid at the inlet pressure is again fed to the high-pressure pump which again pressurises it to at least 10 bar etc.—so that the supply of a liquid jet to the interaction region is effected in a continuous, closed-loop fashion.

It will be appreciated that the above system and method may be utilised, at least in part, for providing the additional liquid in the form of e.g. an additional jet. The system and method may be the same up to the ejection from the nozzle, where the additional jet may be ejected from an additional nozzle. Both nozzles may however be integrated in a structurally common part of the system, which may facilitate their relative alignment.

More generally, a temperature control may be applied. Apart from removing excess heat generated by electron bombardment to avoid corrosion and overheating of sensitive components in the system, there may be a need for heating the liquid in other portions of the system. Heating may be required if the liquid is a metal with a high melting point and the heat power supplied by the electron beam is not sufficient to maintain the metal in its liquid state throughout the system. As a particular inconvenience, if the temperature falls below a critical level, splashes of liquid metal hitting portions of the inner wall of the collection reservoir may solidify and be lost from the liquid circulation loop of the system. Heating may also be required if a large outward heat flow takes place during operation, e.g., if it turns out to be difficult to thermally insulate some section of the system. It should also be understood that heating for start-up may be required if the liquid used is not liquid at typical ambient temperatures. The system may thus comprise both heating and cooling means for adjusting the temperature of the recycled liquid. The additional liquid may in some examples be subject to a separate temperature control, e.g. allowing the additional liquid to be kept at a temperature that is lower than a temperature of the liquid jet upstream of the interaction region.

In some implementations, the X-ray source may be arranged in a system wherein the liquid may be passed through one or more filters during its circulation in the system. For example, a relatively coarse filter may be arranged between the collection reservoir and the high-pressure pump in the normal flow direction, and a relatively fine filter may be arranged between the high-pressure pump and the nozzle in the normal flow direction. The coarse and the fine filter may be used separately or in combination. Embodiments including filtering of the liquid are advantageous in so far as solid contaminants are captured and can be removed from the circulation before they cause damage to other parts of the system.

The technology disclosed may be embodied as computer readable instructions for controlling a programmable computer in such manner that it causes an X-ray source to perform the method outlined above. Such instructions may be distributed in the form of a computer-program product comprising a non-volatile computer-readable medium storing the instructions.

It will be appreciated that any of the features in the embodiments described above for the X-ray source according to the first aspect above may be combined with the method according to the second aspect of the present invention.

Further objectives of, features of, and advantages with the present invention will become apparent when studying the following detailed disclosure, the drawings and the appended claims. Those skilled in the art will realize that different features of the present invention can be combined to create embodiments other that those described in the following.

BRIEF DESCRIPTION OF THE DRAWINGS

The above, as well as additional objects, features and advantages of the present invention, will be better understood through the following illustrative and non-limiting detailed description of embodiments of the present invention. Reference will be made to the appended drawings, on which.

All the figures are schematic, not necessarily to scale, and generally only show parts which are necessary in order to elucidate the invention, wherein other parts may be omitted or merely suggested.

DETAILED DESCRIPTION OF EMBODIMENTS

Figure 1:
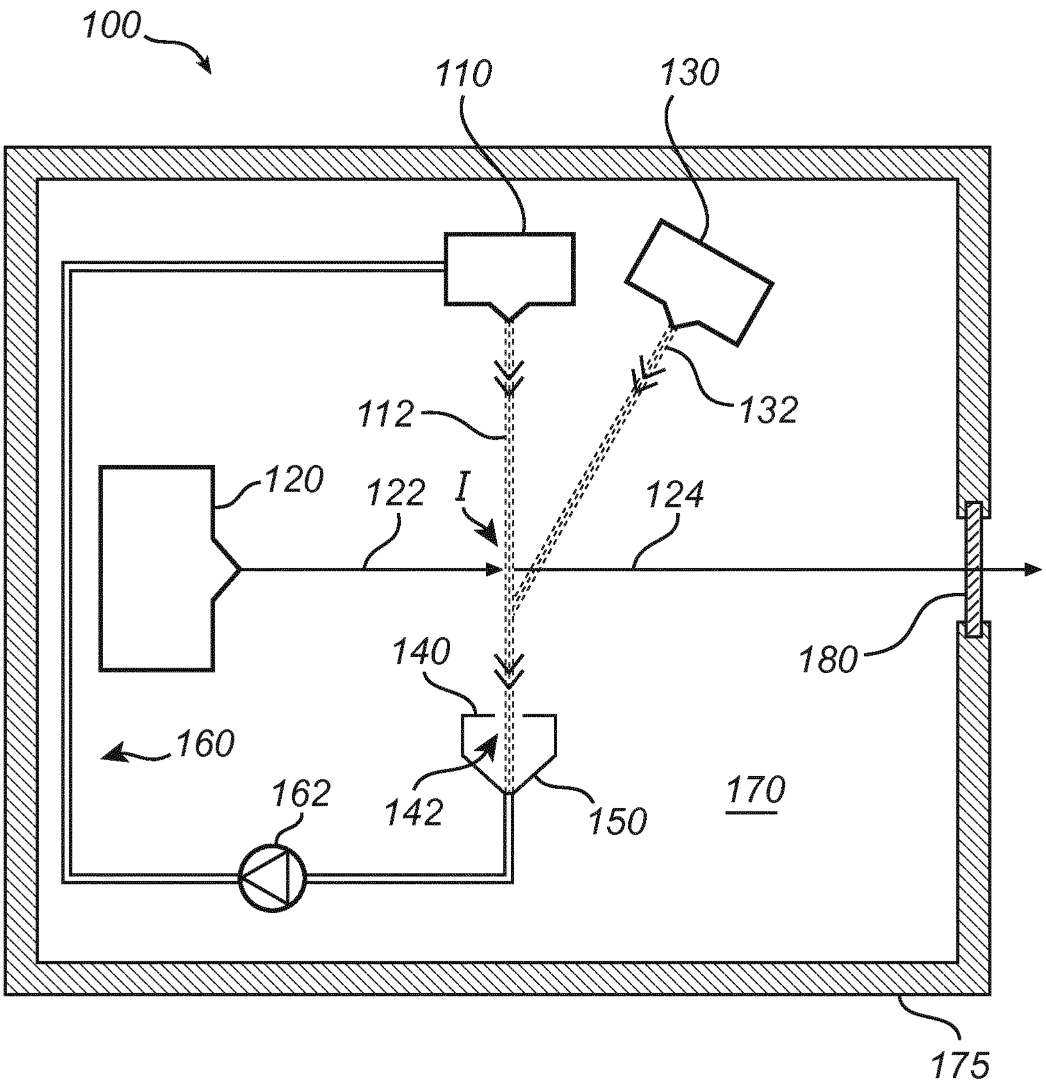
FIGS. 1 to 3 are schematic, cross sectional side views of systems according to some embodiments of the present invention.

A system comprising an X-ray source 100 according to an embodiment of the invention will now be described with reference to FIG. 1. As indicated in FIG. 1, a vacuum chamber 170 may be defined by an enclosure 175 and an X-ray transparent window 180 that separates the vacuum chamber 170 from the ambient atmosphere. The X-rays 124 may be generated from an interaction region I, in which electrons from an electron beam 122 may interact with a target of a liquid jet 112.

The electron beam 122 may be generated by an electron source, such as an electron gun 120 comprising a high-voltage cathode, directed towards the interaction region I.

The interaction region I may be intersected by the liquid jet 112, which may be generated by a target generator 110. The target generator 110 may comprise a nozzle through which liquid, such as e.g. liquid metal may be expelled to form a jet 112 propagating towards and through the interaction region I.

A shield 140, having an aperture 142, may be arranged downstream of the interaction region I such that the liquid metal jet 122 is allowed to pass through the aperture 142. In some embodiments, the shield 140 may be arranged at the end of the liquid metal jet 122, preferably in connection with a collection reservoir 150. Debris, splashes and other particles generated from the liquid metal downstream of the shield 140 may be deposited on the shield and thus prevented from contaminating the vacuum chamber 170.

The system may further comprise a closed-loop circulation system 160 located between the collection reservoir 150 and the target generator 110. The closed-loop system 160 may be adapted to circulate the collected liquid metal to the target generator 110 by means of a high-pressure pump 162 adapted to raise the pressure to at least 10 bar, preferably at least 50 bar or more, for generating the target jet 112.

Further, a mixing tool may be provided for inducing mixing of the liquid metal of the jet 112 at a certain distance downstream of the interaction region I. The mixing tool may e.g. be a liquid metal source 130 for supplying additional liquid 132 to the liquid jet 112 at the said distance. The additional liquid 132 may be provided to induce mixing of the liquid of the jet 112 and/or to absorb or redistribute at least some of the heat induced in the liquid jet 112 by the electrons impinging the interaction region I. The distance is preferably selected such that a maximum surface temperature of the liquid jet 112 downstream of the interaction region I is kept below a threshold temperature so as to reduce the amount of vapour originating from the liquid jet.

In FIG. 1, the additional liquid 132 is supplied in the form of an additional liquid metal jet 132. The additional jet 132 may be formed by an additional nozzle 130 configured to direct the additional jet 132 to intersect the liquid metal jet 112 at a desired position downstream of the interaction region I. Referring to the exemplary embodiment in FIG. 1, the additional jet 132 may be oriented to intersect a plane coinciding with the electron beam 122 and the liquid metal jet 112 so as not to interfere with the electron beam 122 (or shadow the generated X-ray beam 124). It will however be appreciated that other configurations also are conceivable, wherein the additional liquid 132 e.g. is supplied in the form of a liquid curtain intersecting with the liquid metal jet 112. The liquid curtain (or liquid veil or film) may e.g. be formed by a slit-shaped additional nozzle 130 or an array of nozzles 130 generating an array of additional jets 132 merging into a substantially continuous curtain or sheet of liquid metal.

Figure 2:
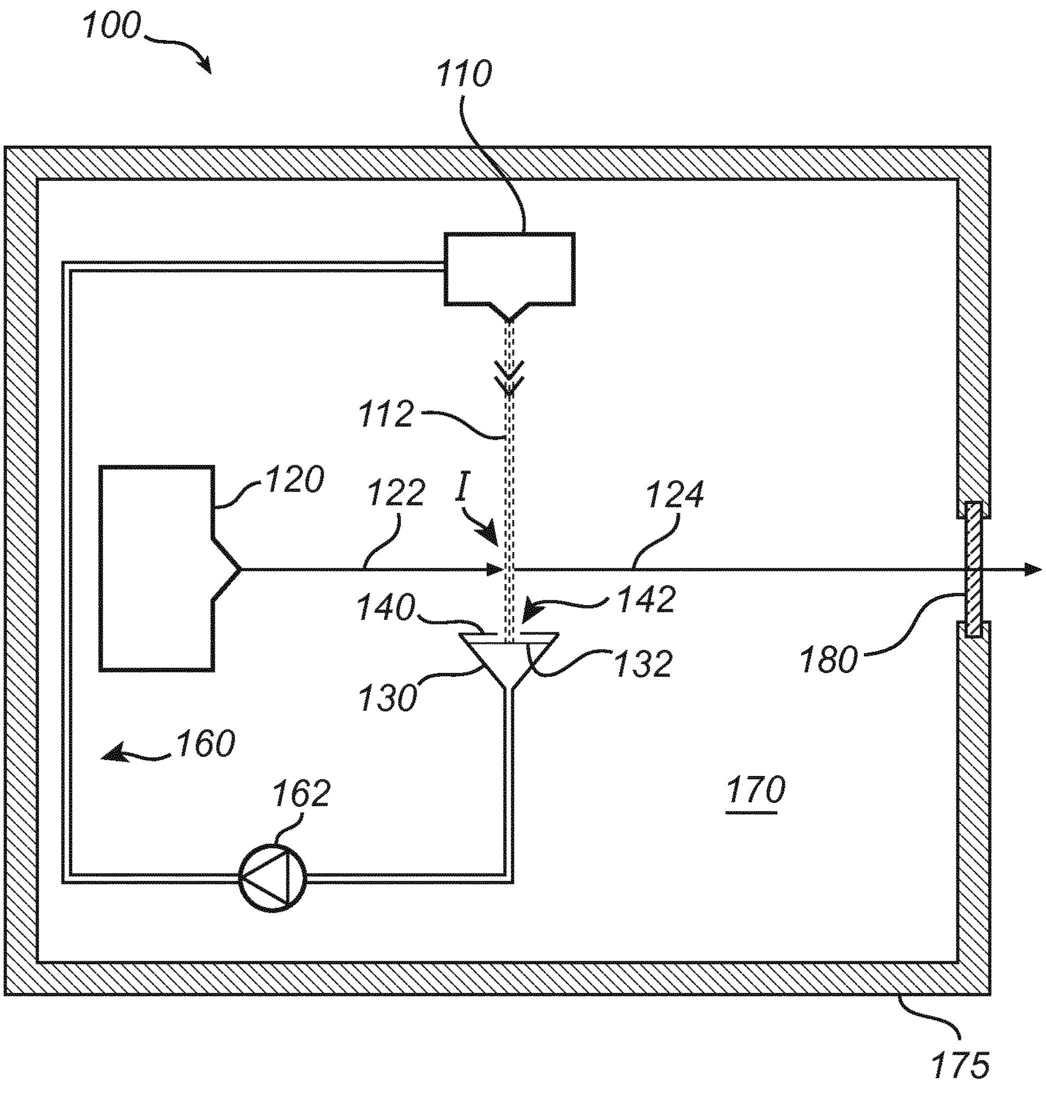

FIG. 2 discloses a similar system as the one described with reference to FIG. 1. However, in the present embodiment the liquid source 130 is realised by a pool 130 of additional liquid, such as liquid metal 132, arranged such that a surface of the pool 130 intersects the liquid metal jet 112 at the desired position downstream of the interaction region I to keep the maximum surface temperature below the threshold. As indicated in FIG. 2, the pool 130 may be combined with a collection reservoir 150 for collecting the liquid metal at the end of the liquid metal jet 112, and a shield 140. The shield 140 may be arranged such that the aperture 142 is located between the interaction region I and surface of the pool 130. The pool 130 may further comprise a sensor for measuring the level of the additional liquid metal 132 of the pool, and a level controlling device for controlling said level based on output from the sensor (sensor and level controlling device not shown in FIG. 2).

Figure 3:
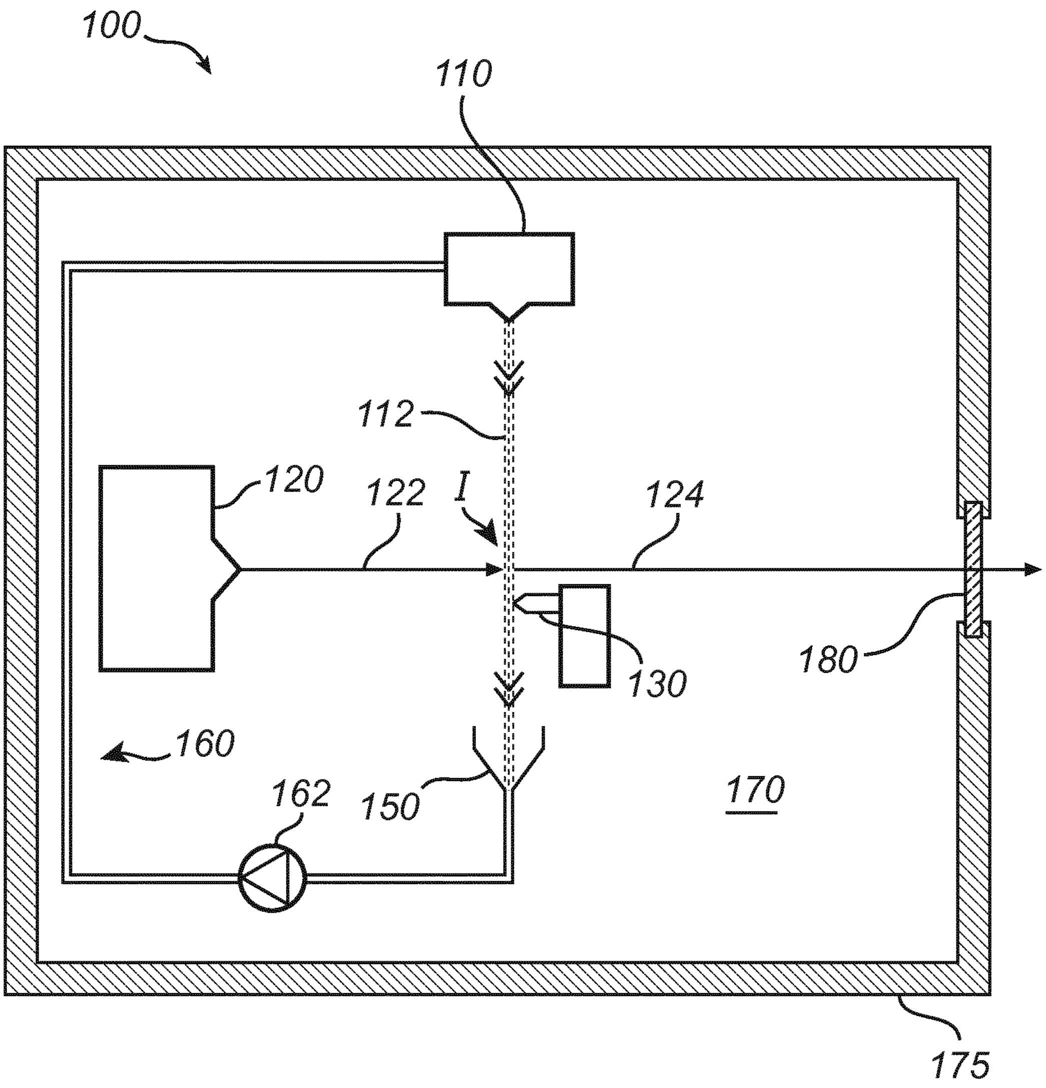

FIG. 3 shows a further embodiment of a system that may be similarly configured as the embodiments described with reference to FIGS. 1 and 2. According to this embodiment, the system may comprise a mixing tool 130 arranged to interact or interfere with the liquid jet 112 such that mixing of the liquid jet is induced at a certain distance downstream of the interaction region I. The certain distance, or point of mixing, may correspond to the position in which the additional liquid 132 is supplied to the liquid jet 112 according to the embodiments of FIGS. 1 and 2. The mixing tool 130 may e.g. comprise an edge being inserted into at least a portion of the propagating liquid jet 112, or be formed by a surface onto which the entire jet 112 or at least a part of the jet 112 is impacting so as to induce mixing within the liquid of the jet 112. The mixing may also be realised, or induced, by supply of an additional liquid metal 132 as described above in connection with FIGS. 1 and 2.

The above-discussed embodiments may be combined with the shield 140 described with reference to FIG. 1. The shield 140 may be arranged downstream of the position in which the additional liquid metal 132 is supplied to the liquid metal jet 112 and/or in which the mixing is induced. However, it will be appreciated that the shield 140, according to alternative embodiments, may be arranged such that the aperture 142 is located between the interaction region I and the position for supply of the additional liquid metal 132 and/or the position at which mixing may be induced.

Figure 4:
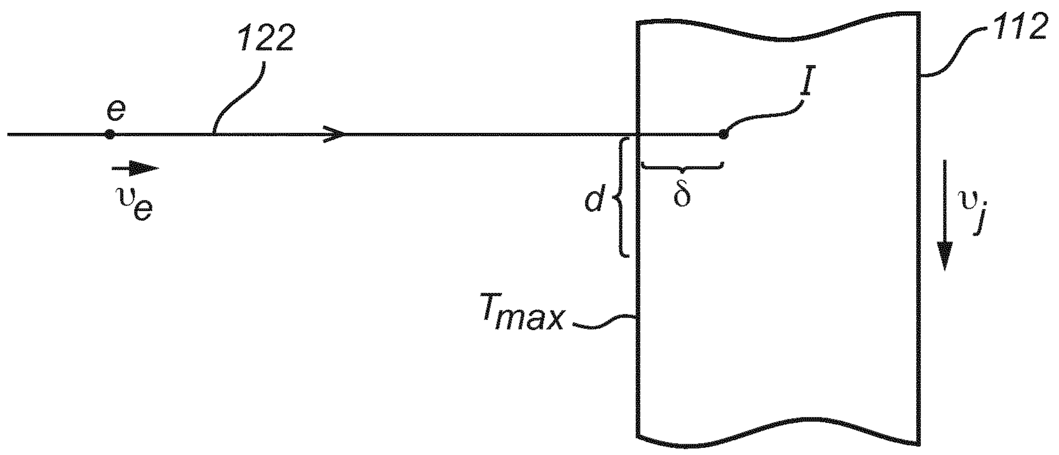
FIG. 4 illustrates the interaction region in a portion of a liquid jet according to an embodiment.

FIG. 4 illustrates a cross sectional side view of a portion of the liquid jet 112 according to any one of the previously described embodiments. In this example, the liquid jet 112 propagates through the interaction region I at speed $v_j$. Further, an electron beam 122 is illustrated, in which electrons propagate towards the liquid jet at speed $v_e$ and interacts with the liquid of the jet 112 in the interaction region I. The penetration depth of the electrons into the jet 112 is in the present FIG. 4 indicated by δ. In the following, an example of how to estimate the position of the maximum surface temperature of the jet is given. It should however be noted that this is merely an example based on a physical model for illustrating the underlying heat diffusion process resulting in the maximum surface heat of the jet being located at a certain distance downstream of the interaction region. It should also be noted that this model may not be applicable for cases wherein the temperature within the liquid jet exceeds the boiling point of the liquid jet. Other methods of determining the distance between the interaction region I and the position having the maximum surface temperature are conceivable.

The electrons impacting the liquid jet 112 may have a characteristic penetration depth δ that depends, inter alia, on the energy of the impacting electrons. The time it will take for the electrons to penetrate the liquid depends e.g. on the scattering events they experience. A conservative estimate of this time may be obtained by using the incoming electron velocity $v_e$. The estimate can be improved by considering the amount of scattering essentially perpendicular to the incoming direction of the electrons. This gives the following relation:

$$\delta = \frac{0.1E_0^{1.5}}{\rho}$$

where $E_0$ is the energy of the incoming electrons in keV, ρ is the target density in g/cm$^3$, and δ is the penetration depth in μm. The width of the interaction volume can in a similar approximation be written as $$y = \frac{0.077E_0^{1.5}}{\rho}$$

where y is in μm. Thus, the electrons may be distributed within a cone having an angle of $\tan^{-1}(0.077/(2\times0.1))$ from the incoming direction. If the incoming linear momentum is partitioned accordingly the resulting velocity in the forward direction is the cosine of this angle times the incoming velocity. Thus the velocity in the impact direction can be estimated as 93% of the velocity of the incoming electrons. To calculate the velocity of the electrons from the acceleration voltage, relativistic effects might have to be considered. According to special relativity the velocity of an electron with energy $E_0$ keV can be written as $$v = c\sqrt{1 - \frac{1}{\left(1 + \frac{E_0}{511}\right)^2}}$$

where c is speed of light in m/s, the rest mass of the electron has been set to 511 keV, and v is in m/s. Putting all of this together gives the following estimate for the time required for electrons to penetrate into the jet:

$$\tau_e = \frac{\delta}{0.93 v_e} = \frac{\frac{0.1 E_0^{1.5}}{\rho}}{0.93c\sqrt{1 - \frac{1}{\left(1 + \frac{E_0}{511}\right)^2}}},$$

where $\tau_e$ is in μs.

The time required for the heat to reach the surface of the jet and thus cause vaporization of the liquid can be estimated by solving the heat equation $$\frac{\partial T}{\partial t} = \alpha \nabla^2 T,$$

where the temperature T is a function of time and three spatial dimensions (x, y, and z), α is the heat diffusivity in units of $m^2/s$. If an initial temperature distribution corresponding to a temperature elevation ΔT in a point at a distance δ into the liquid jet is assumed one may write the excess temperature as $$T = \Delta T \frac{1}{(4\pi\alpha t)^{3/2}} e^{-\frac{x^2+y^2+z^2}{4\alpha t}}.$$

By seeking the time where this function reaches its maximum for a spatial coordinate corresponding to the jet surface an estimate on the time when maximum evaporation rate occurs can be obtained. By selecting the coordinate system so that (x,y,z)=(δ,0,0) on a point on the jet surface closest to the point where the initial elevated temperature is applied, deriving T with respect to t, and setting the derivative to zero one obtains $$\tau_T = \frac{\delta^2}{6\alpha}$$

where $\tau_T$ is the time when temperature on the jet surface reaches its maximum.

The distance from the interaction point until maximum jet surface temperature occurs can thus be written as $$d = v_J(\tau_T + \tau_e) = v_J\left(\frac{\delta^2}{6\alpha} + \frac{\delta}{v_e^{\perp}}\right) = v_J\delta\left(\frac{\delta}{6\alpha} + \frac{1}{v_e^{\perp}}\right)$$

where $v_e^{\perp}$ is the electron velocity inside the jet in the direction perpendicular to the jet surface. By applying the expressions for penetration depth and electron velocity from above this can further be written as $$d = v_J \frac{0.1 E_0^{1.5}}{\rho}\left(\frac{10^{-7} E_0^{1.5}}{6\alpha\rho} + \frac{1}{0.93c\sqrt{1 - \frac{1}{\left(1 + \frac{E_0}{511}\right)^2}}}\right)$$

where again ρ should be in $g/cm^3$, $E_0$ in keV, and d is in μm. By inserting realistic values for a liquid gallium jet X-ray source (ρ=6 $g/cm^3$, $\alpha \approx 1.2 \times 10^{-5}$ $m^2/s$, $E_0$=50 keV, $v_j$=100 m/s) a distance of about 50 μm is obtained. If the electron energy can be raised to 100 keV the distance would, according to this example, increase to almost 400 μm; if the jet velocity can be increased to 1000 m/s in the same setting the distance may increase to close to 4 mm.

It turns out that for most practical purposes the second term in the parenthesis above, corresponding to the time it takes for the electrons to reach their penetration depth, gives a negligible contribution. For simplicity we can thus estimate the distance d as $$d \approx v_J \frac{E_0^3}{6\alpha\rho^2} 10^{-8}.$$

Figure 5:
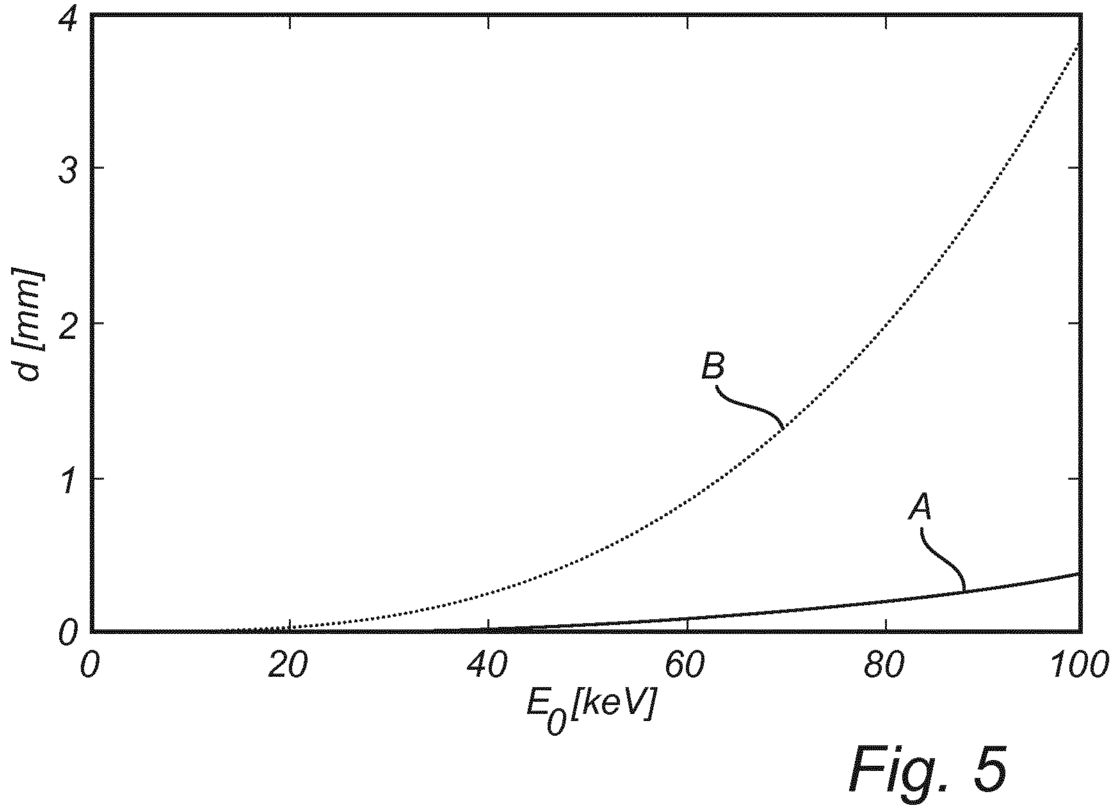
FIG. 5 is a diagram illustrating the distance between the interaction region and the position of the maximum surface temperature as a function of the energy of the impacting electrons.

The relation between electron energy and distance d according to this model is illustrated in the FIG. 5, which shows, for two different velocities $v_j$ of the liquid jet, the distance d (in mm) between the interaction region and the location of the maximum surface temperature $T_{max}$ (i.e., when no additional liquid or mixing is employed) as a function of the electron energy $E_0$ (in keV). Curve A represents the distance d for the exemplary system described above, i.e., for ρ=6 $g/cm^3$, $\alpha \approx 1.2 \times 10^{-5}$ $m^2/s$ and a liquid jet velocity $v_j$ of 100 m/s. As indicated, this may result in a distance d of about 50 μm for electron energies of 50 keV and a distance d about 0.4 mm for electron energies of 100 keV. Increasing the velocity $v_j$ of the liquid jet to 1000 m/s would, according to the present model as represented by curve B, result in a distance d of about 0.5 mm for electron energies of 50 keV and a distance d of about 3.8 mm for electron energies of 100 keV. This relation, or other estimations of the distance d, may be employed to determine where on the propagating jet to supply the additional liquid so as to prevent the maximum surface temperature from exceeding the threshold value. The additional liquid may in other words be supplied at a position between the interaction region and the estimated distanced so as to reduce the maximum surface temperature. Examples of suitable distances may be included in the range of 50 μm to 4 mm.

Figure 6A:
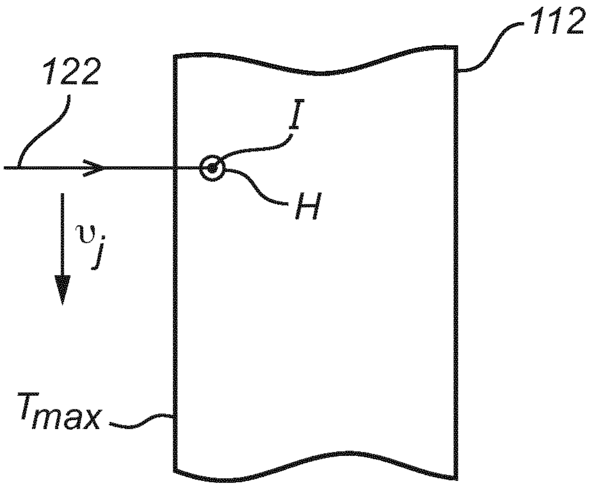
FIGS. 6*a* to *d* illustrate the propagation of the heat induced in the interaction region according to an embodiment.
Figure 6B:
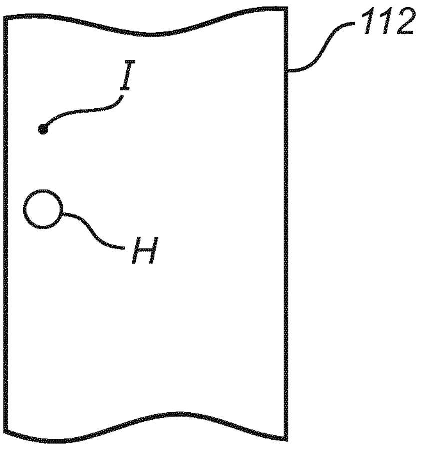
Figure 6C:
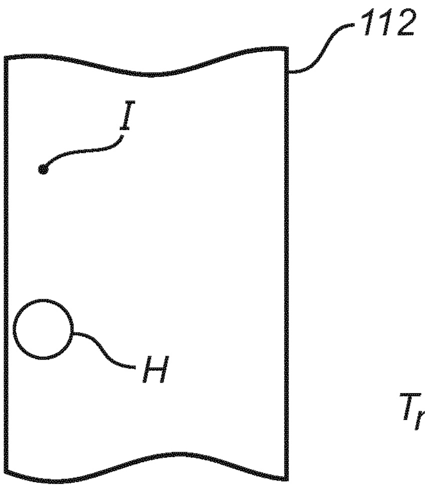
Figure 6D:
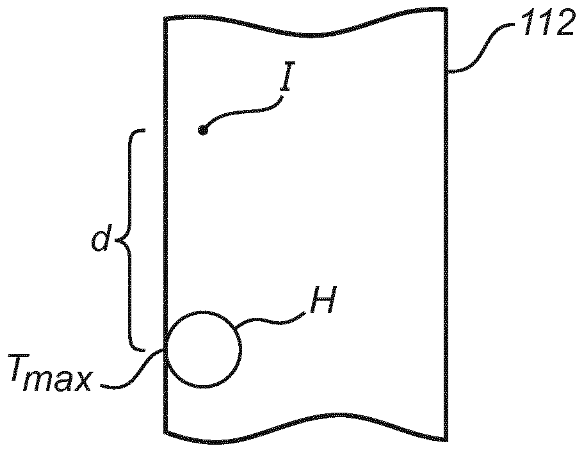

FIGS. 6*a* to *d* are a sequence of figures illustrating the diffusion over time of the heat induced in the interaction region I by the impacting electrons. Similar to FIG. 4, FIGS. 6*a* to *d* show a cross sectional side view of a portion of the liquid jet 112 according to an embodiment of the present invention. The expansion and propagation of the heated portion or region H of the liquid is indicated in relation to the position of the interaction region I. FIG. 6*a* illustrates the heated region H shortly after impact, showing a relatively small region H located at the interaction region I. Over time, the heated region expands due to heat diffusion, and propagates downwards with the velocity $v_j$ of the jet 112. This is illustrated in FIGS. 6*b* and *c*, showing a slightly increasing region H being located further and further downstream of the interaction region I. Finally, in FIG. 6*d*, the heated region H has expanded all the way to the surface of the jet 112. This occurs at the distance d downstream of the jet, wherein the surface reaches its maximum temperature $T_{max}$ and, accordingly, its vaporisation maximum. Thus, by inducing mixing, e.g. by supplying the additional liquid, at a position upstream of the position where the maximum temperature $T_{max}$ otherwise would occur, the vaporisation from the exposed surface may be reduced.

According to an example, the threshold temperature may be based on the vapour pressure for the particular type of liquid used in the vacuum chamber. For a liquid metal jet exposed to a typical vacuum chamber pressure of $5\times10^{-7}$ mbar, this would result in a temperature of about 930 K for Ga, 1015 K for Sn, 850 K for In, 660 K for Bi and about 680 K for Pb. Thus, for a chamber pressure of $5\times10^{-7}$ mbar, mixing of the liquid metal jet may preferably be provided such that the maximum surface temperature of the liquid metal jet is kept below the above mentioned temperatures so as to reduce vaporisation of the liquid metal.

Figure 7:
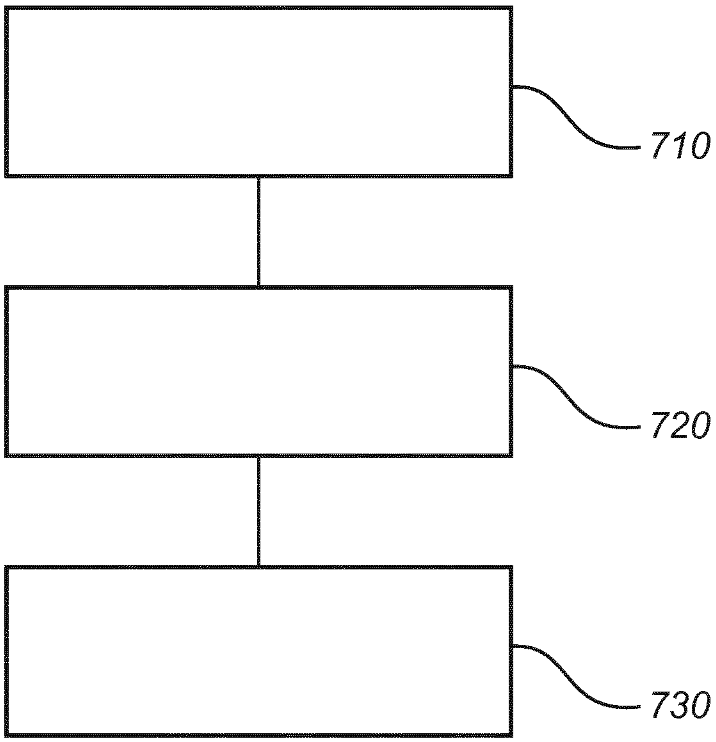
FIG. 7 is a flowchart of a method according to an embodiment of the present invention.

FIG. 7 is a flowchart illustrating a method for generating X-ray radiation according to an embodiment of the present invention. The method may comprise the steps of forming 710 a liquid jet propagating through an interaction region, directing 720 an electron beam towards the liquid jet such that the electron beam interacts with the liquid jet at the interaction region to generate X-ray radiation, and supplying 730 additional liquid to the liquid jet at a distance downstream of the interaction region such that a maximum surface temperature of the jet downstream of the interaction region is below a threshold temperature.

The person skilled in the art by no means is limited to the example embodiments described above. On the contrary, many modifications and variations are possible within the scope of the appended claims. In particular, X-ray sources and systems comprising more than one electron beam and/or liquid jets are conceivable within the scope of the present inventive concept. Additionally, variation to the disclosed embodiments can be understood and effected by the skilled person in practising the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. An X-ray source comprising:

a target generator adapted to form a liquid jet propagating through an interaction region;

an electron source adapted to provide an electron beam directed towards the interaction region such that the electron beam interacts with the liquid jet to generate X-ray radiation; and a mixing tool adapted to induce mixing of the liquid jet at a distance downstream of the interaction region such that a maximum surface temperature of the liquid jet downstream of the interaction region is below a threshold temperature.

2. The X-ray source according to claim 1, wherein the threshold temperature corresponds to the temperature when the vapour pressure of the liquid jet equals a pressure exerted on the liquid jet.

3. The X-ray source according to claim 1, further comprising a shield arranged downstream of the interaction region, wherein the shield comprises an aperture arranged to allow the liquid jet to pass through the aperture.

4. The X-ray source according to claim 3, wherein the aperture is arranged within said distance from the interaction region.

5. The X-ray source according to claim 3, wherein the shield is arranged on a collection reservoir for collecting the liquid jet.

6. The X-ray source according to claim 5, further comprising a closed-loop circulation system located between the collection reservoir and the target generator and adapted to circulate the collected liquid of the liquid jet to the target generator.

7. The X-ray source according to claim 3, further comprising a sensor for detecting contamination, originating from the liquid, on a side of the shield facing away from the interaction region.

8. The X-ray source according to claim 1, wherein the mixing tool is formed of a surface arranged to intersect with the liquid jet.

9. The X-ray source according to claim 1, wherein the mixing tool is a liquid source adapted to supply an additional liquid to the liquid jet.

10. The X-ray source according to claim 9, wherein the liquid source is formed by a pool of the additional liquid.

11. The X-ray source according to claim 9, further comprising:

a sensor for measuring a level of the additional liquid of the pool; and a level controlling device for controlling said level based on output from the sensor.

12. The X-ray source according to claim 9, wherein the liquid source is adapted to supply the additional liquid in the form of an additional jet.

13. The X-ray source according to claim 12, wherein a velocity of the additional jet comprises a non-negative component in respect to a travelling direction of the liquid jet.

14. The X-ray source according to claim 9, wherein the liquid source is adapted to supply the additional liquid in the form of a liquid curtain intersecting with the liquid jet.

15. The X-ray source according to claim 9, wherein the liquid source is adapted to provide the additional liquid on a slanting surface arranged to intersect with the liquid jet.

16. The X-ray source according to claim 9, wherein the additional liquid is a liquid metal.

17. The X-ray source according to claim 1, wherein the liquid jet is a liquid metal jet.

18. A method for generating X-ray radiation, comprising the steps of:

forming a liquid jet propagating through an interaction region; directing an electron beam towards the liquid jet such that the electron beam interacts with the liquid jet at the interaction region to generate X-ray radiation; and inducing, by a mixing tool, mixing of the liquid jet at a distance downstream of the interaction region such that a maximum surface temperature of the liquid jet downstream of the interaction region is below a threshold temperature.

19. The method according to claim 18, wherein the step of inducing mixing comprises the step of determining the distance based on at least one of:

a penetration depth of the electron beam into the liquid jet;

a velocity of the jet;

an electron velocity within the liquid jet;

a boiling point of the liquid jet;

a vapour pressure of the liquid jet; and a heat diffusivity of the liquid jet.

* * * * *